United States Patent
Gale et al.

(10) Patent No.: US 6,958,140 B2
(45) Date of Patent: Oct. 25, 2005

(54) METHODS OF IMAGING AND TARGETING VASCULATURE

(75) Inventors: Nicholas W. Gale, Tarrytown, NY (US); George D. Yancopoulos, Yorktown Heights, NY (US)

(73) Assignee: Regeneron Pharmaceuticals, Inc., Terrytown, NY (US)

( * ) Notice: Subject to any disclaimer, the term of this patent is extended or adjusted under 35 U.S.C. 154(b) by 403 days.

(21) Appl. No.: 10/055,842

(22) Filed: Jan. 23, 2002

(65) Prior Publication Data

US 2002/0119097 A1 Aug. 29, 2002

Related U.S. Application Data

(60) Provisional application No. 60/264,406, filed on Jan. 26, 2001.

(51) Int. Cl.[7] .................. A61K 51/00; A61M 36/14
(52) U.S. Cl. .................. 424/9.1; 424/1.11; 424/1.65; 424/1.69; 424/1.73
(58) Field of Search .................. 424/1.11, 1.49, 424/1.65, 1.69, 9.1, 9.2, 9.3, 9.4, 9.5, 9.6, 9.7, 9.8, 800–809, 130.1; 206/223, 569, 570; 530/300, 350, 387.1, 387.2, 388.1; 536/22.1; 544/313

(56) References Cited

U.S. PATENT DOCUMENTS

2002/0136726 A1 * 9/2002 Anderson et al. ........ 424/146.1

OTHER PUBLICATIONS

Kirsch, JE, 1991, "Basic principles of magnetic resonance contrast agents", Top Magn Reson Imaging 3:1–18.
Wallis, F. and Gilbert, FJ, 1999, J R, "Magnetic resonance imaging in oncology: an overview", Coll Surg Edinb 44:117–125.

Schiepers, C. and Hoh, CK, 1998, "Positron emission tomography as a diagnostic tool in oncology", Eur Radiol 8:1481–1494.

Ferrand, SK, et al., 1999, "What is new in nuclear medicine imaging?", Surg Oncol Clin N Am 8:185–204.

Wang, H.U., et al., 1998, "Molecular distinction and angiogenic interaction between embryonic arteries and veins revealed by ephrin–B2 and its receptor Eph–B4", Cell 93:741–753.

Gerety, S.S., et al., 1999, "Symmetrical mutant phenotypes of the receptor EphB4 and its specific transmembrane ligand ephrin–B2 in cardiovascular development", Mol Cell 4:403–414.

Adams, R.H., et al., 1999, "Roles of ephrinB ligands and EphB receptors in cardiovascular development: demarcation of arterial/venous domains, vascular morphogenesis, and sprouting angiogenesis", Genes & Dev 13:295–306.

* cited by examiner

Primary Examiner—Dameron L. Jones
(74) Attorney, Agent, or Firm—Valeta Gregg, Esq.

(57) ABSTRACT

Methods for imaging and targeting tumor vasculature are provided. Specifically, the methods for imaging and targeting tumor vasculature relate to using ephrin-B2 to image developing tumor vasculature and to target therapeutic agents to developing tumor vasculature. Kits for imaging and targeting tumor vasculature are also provided. Also provided for are methods of delivering agents to vasculature.

9 Claims, 1 Drawing Sheet

METHODS OF IMAGING AND TARGETING VASCULATURE

This application claims priority to U.S. Provisional Application Ser. No. 60/264,406 filed Jan. 26, 2001. Throughout this application various publications are referenced. The disclosures of these publications in their entireties are hereby incorporated by reference into this application.

FIELD OF THE INVENTION

The field of this invention is methods of imaging and targeting tumor vasculature. Specifically, the field of this invention relates to using ephrin-B2 to image developing tumor vasculature. It also relates to using ephrin-B2 to target chemotherapeutic agents to developing tumor vasculature.

BACKGROUND

The lack of improvement in cure rate of many common tumors is amply documented and often ascribed to failure of early detection. Present clinical means for detecting tumor tissue remain in many instances a gross anatomic procedure relying upon various physical findings or radiographic imaging procedures to select a site for histologic sampling. Scintillation imaging techniques with radiopharmaceuticals such as $^{67}$Ga-Gallium citrate, $^{111}$In-Bleomycin and $^{131}$I-Diiodofluorescein have limited success. These radiolabeled compounds lack specificity and sensitivity, that is, they are not preferentially taken up by tumors. Both $^{67}$Ga-Gallium citrate and $^{111}$In-Bleomycin are accumulated in inflammatory or infectious lesions. Currently, all available diagnostic techniques have many drawbacks and limitations in addition to lack of sensitivity and specificity. These include the use of traumatic invasive procedures and the potential for serious complications.

Attempts to "mark" or "tag" tumor cells in order to differentiate them from normal tissues are not new. Various fluorescent compounds such as porphyrins, tetracycline derivatives, acridine orange and toluidine blue or radioactive isotopes have been extensively investigated. With the exception of porphyrin compounds, none of these substances used by earlier investigators are capable of routinely identifying and delineating tumors and tumor margins.

To be effective, an ideal marker substance should: (1) be safe and nontoxic in humans; (2) selectively accumulate only in tumor tissue and not be taken up by normal or inflammatory tissues; (3) be simple to use and involve non-invasive procedures; and (4) be capable of being documented by photographs, radiographs or other recording devices. Unfortunately, the ideal marker or tracer continues to remain elusive.

Technetium-99 m ($^{99}$mTc) based radiopharmaceuticals have been widely used in the past 15 years. They are by far the safest and the most useful scintigraphic imaging agents developed for Nuclear Medicine procedures. The radionuclide $^{99}$mTc has many advantages. It is a pure gamma emitter with a relatively short physical half life of six hours. The gamma photon of 140 KeV energy is compatible with existing conventional scintillation imaging equipment. $^{99}$mTc-radiopharmaceuticals can be administered to patients in a much larger dose than many other radiolabeled compounds but produces a minimal radiation health hazard.

For the non-invading nuclear medical diagnosis of tumor, there is ordinarily used gallium citrate ($^{67}$Ga). While ($^{67}$Ga) has an accumulating property on tumor cells, it simultaneously possesses the following disadvantages: (1) since its specificity to tumor cells is low and its energy characteristics are not proper, clear and sharp scintigraphy is hardly obtainable; (2) it takes a long time until the radioactivity disappears from the entire body so that many days are needed for the examination; and (3) its half life is 78.1 hours, and the amount of exposure dose against the patient can not be disregarded. For the above reasons, much research has been done to develop an imaging agent having a high specificity to tumor cells to make a quick diagnosis possible.

One of the recent proposals is imaging of tumor cells using a radioisotope-labeled antibody with a high specificity to tumor cell markers. Since the large scale production of a monoclonal antibody by cell culture of hybridoma cells was reported by Milstein et al. (Nature, Vol. 256, p. 495 (1975)), various antibodies specific to tumor-related antigens have been produced, and imaging of tumor cells using these monoclonal antibodies has been extensively tested. The imaging technique using a radioisotope-labeled antibody is generally called a "radioimmunosintigraphy". Unfortunately, this technique also has inherent problems. For instance, the radioisotope-labeled antibody takes a long time to accumulate on tumor cells and the up-take ratio by these cells is low. Further, the accumulation is done not only by tumor cells, but also by normal organ and tissue cells, and the disappearance of the radioactivity from these organs and tissues takes a long time. For these reasons this technique is has proven impractical.

Studies on the diagnosis of breast cancer have been done with substances specific to steroid hormone receptors such as radioactive iodine-labeled estradiol derivatives (Hanson et al.: American Chemical Society Meeting, Aug. 3–28, 1981, Reference N.U.S.L. 56; Kabalka: Applications of Nuclear and Radiochemistry, Lambrecht, R. M. Morcosn., Eds., Newark, N.J., Pergamon Press, 1981, Chap. 17; JP-A-60-78995). In order to achieve a reliable diagnosis with these receptor-specific substances, the substances are required to satisfy the following conditions: (1) they have to exhibit high affinity and specificity to the receptor; (2) their specific radioactivity must be sufficiently high; and (3) their labeling nuclide must not be liberated in the body. Unfortunately, radioactive receptor-specific substances satisfying all these conditions have not yet been developed.

Various attempts have been made to identify specific tumor sites by simple techniques. For example, it would be desirable to identify the location of tumor cells by localization of a particular tumor marker at the specific tumor site. It would also be desirable to target the specific tumor site with chemotherapeutic agents by introducing substances into the patient's body that are directed to the tumor marker and that deliver a chemotherapeutic agent to the specific tumor site. In spite of such attempts, however, simple delivery systems for targeting tumors in humans do not as yet exist.

Administering a chemotherapeutic agent usually harms many of the normal body cells, often resulting in a worsening of the patient's condition without achieving the desired reduction in tumor size. Historically, this toxicity to normal cells has been a major disadvantage in the treatment of tumors with chemotherapeutic agents. The lack of efficacy of chemotherapy is also attributed to the failure of the freely circulating drug to localize within the tumor cells before it is excreted or taken up by other cells in the body.

Prior attempts to improve treatment of tumors by chemotherapeutic agents includes encapsulation of such chemotherapeutic agents within biodegradable phospholipid micellar particles in the form of vesicles or liposomes.

Encapsulation is thought to reduce the toxicity caused by the circulating chemotherapeutic agents. Researchers have also sought to utilize encapsulation to selectively target tumors for delivery of chemotherapeutics agents. Unfortunately, efforts to localize or treat tumors with chemotherapeutic agent-encapsulated targeting particles have not been overly successful.

Localization of tumors such as astrocytomas in the brain in vivo and the determination of the margin between normal tissue and tumor can be useful for surgical, radiotherapeutic and chemotherapeutic approaches to treating the tumor. Although gliomas generally do not metastasize, they do recur locally after surgical resection and carry a grave prognosis. The grave prognosis results in part from the inability to delineate clearly the boundary between tumor and normal brain tissue, and from the restricted permeability of the blood brain barrier to imaging and chemotherapeutic agents.

Monoclonal antibodies prepared against tumors have been proposed for use in the past as effective carrier molecules for the delivery of contrast and radionuclide agents. However, the use of such monoclonal antibodies is accompanied by disadvantages. Antibodies are very large molecules that also can carry cross-reactive antigenic determinants that could cause problems. In addition, the monoclonal antibodies seldom bind more than 70% of cells, even in clonogenic tumors.

In addition to monoclonal antibodies, various synthetic polypeptides, such as polylysine which selectively binds to tumor cells as compared to normal brain cells, have been considered for use as carrier agents for chemotherapeutic agents. Clearly, a need still exists for reliable, safe methods for the imaging, targeting, and treatment of tumors and for substances that can be used in such methods.

In an attempt to satisfy this long felt need, Applicants turned to a family of receptor tyrosine kinases and their cognate ligands that are expressed in the body in particular patterns as candidate molecules for imaging, targeting, and treating tumors. This family, known as the Eph receptor tyrosine kinases, comprise the largest known family of growth factor receptors, and utilize the similarly numerous ephrins as their ligands (Flanagan and Vanderhaeghen, 1998; Gale and Yancopoulos, 1997). The ephrins are unlike ligands for other receptor tyrosine kinases in that they must be membrane-tethered in order to activate their Eph receptors (Davis et al., 1994; Gale and Yancopoulos, 1997). The obligate membrane-attachment of the ephrins provided the first clue that they might act precisely at points of cell-to-cell contact. Based on their means of tethering to the cell membrane, the ephrins can be subdivided into two subclasses. The five members of the ephrin-A subclass (ephrin-A1 to A5) are attached to the outer leaflet of the plasma membrane via a glycosylphosphatidylinositol (GPI) anchor, whereas the three members of the ephrin-B subclass (ephrin-B1 to B3) have a transmembrane region and highly conserved cytoplasmic domains. Ephrin-B ligands primarily interact with the B subset of Eph receptors, consisting of at least six members (Flanagan and Vanderhaeghen, 1998; Gale and Yancopoulos, 1997; Gale and Yancopoulos, 1999). Interactions between ephrin-B ligands and EphB receptors apparently activate bidirectional signaling, in that the cytoplasmic domains of not only the engaged receptor but also of the interacting ligand become phosphorylated on tyrosine residues (Bruckner et al., 1997; Holland et al., 1996).

The ephrins and Ephs were initially studied for their actions in the nervous system, where they seem to play important roles in axonal guidance and in neuronal patterning (Flanagan and Vanderhaeghen, 1998; Gale and Yancopoulos, 1997). More recent studies have begun to focus on roles of these molecules outside of the nervous system. ephrin-B2 and its cognate EphB4 receptor have recently attracted attention in the field of cardiovascular development, based on the vascular defects observed in embryonic mice bearing null mutations in the genes for this ligand and receptor pair (Adams et al., 1999; Gerety et al., 1999; Wang et al, 1998). Normal vascular development initiates with a vasculogenic phase that involves formation of a primitive vascular scaffold, followed by angiogenic stages during which this early vasculature undergoes remodeling and maturation (Risau, 1997). Mouse embryos lacking ephrinB2 and EphB4 suffer fatal defects in early angiogenic remodeling (Adams et al., 1999; Gerety et al., 1999; Wang et al., 1998). Moreover, ephrin-B2 and EphB4 display a remarkably reciprocal pattern of distribution within the developing vasculature—that is, ephrin-B2 marks the endothelium of primordial arterial vessels while EphB4 marks the endothelium of primordial venous vessels (Adams et al., 1999; Gerety etal., 1999; Wang 1998). These distributions suggested that ephrin-B2 and EphB4 are involved developmentally in establishing arterial versus venous identity, perhaps in joining arterioles to venules, and that defects in these processes might account for the early lethality observed in mouse embryos lacking these proteins (Adams et al., 1999; Gale and Yancopoulos, 1999; Gerety et al., 1999; Wang et al., 1998; Yancopoulos et al., 1998).

Despite the remarkably reciprocal distributions of ephrin-B2 and EphB4 during very early vascular development, little is known about the distribution or functions of these proteins as vascular development proceeds, in the quiescent adult vasculature, or when angiogenesis is reinitiated in the adult such as in tumors or in the female reproductive system. To explore these issues, Applicants have exploited a genetically engineered mouse in which the LacZ coding region is used to substitute and report for the ephrin-B2 coding region.

SUMMARY OF THE INVENTION

In adult settings of angiogenesis, as in tumors or in the female reproductive system, the endothelium of a subset of new vessels strongly expresses ephrin-B2, suggesting that ephrin-B2 plays an important role during the development of arteries, perhaps by regulating endothelialsmooth muscle interactions involved in the formation of the muscle wall. Thus, ephrin-B2 appears to be an early marker in adult settings of angiogenesis and, therefore, is likely to be useful in the imaging of very small tumors and metastases and in methods designed to specifically target chemotherapeutic agents to tumor vasculature.

The subject invention provides for a method for imaging tumor vasculature in a mammal comprising administering to the mammal a composition which comprises a molecule capable of detecting ephrin-B2 nucleic acid or polypeptide coupled to an imaging agent; allowing the composition to accumulate at the tumor vasculature; and detecting the accumulated composition so as to image the tumor vasculature.

The subject invention also provides for a method of causing tumor cell death by targeting tumor vasculature comprising administering to a mammal a composition which comprises a molecule capable of detecting ephrin-B2 nucleic acid or polypeptide coupled to an agent capable of causing tumor cell death.

The subject invention further provides for a method of causing vascular endothelial cell death by targeting tumor vasculature comprising administering to a mammal a composition which comprises a molecule capable of detecting ephrin-B2 nucleic acid or polypeptide coupled to an agent capable of causing vascular endothelial cell death.

In addition, the subject invention provides for a kit for imaging tumor vasculature in a mammal comprising a composition which comprises a molecule capable of detecting ephrin-B2 nucleic acid or polypeptide coupled to an imaging agent; a kit for targeting tumor vasculature in a mammal comprising a composition which comprises a molecule capable of detecting ephrin-B2 nucleic acid or polypeptide coupled to an agent capable of causing tumor cell death; and a kit for targeting tumor vasculature in a mammal comprising a composition which comprises a molecule capable of detecting ephrin-B2 nucleic acid or polypeptide coupled to an agent capable of causing vascular endothelial cell death.

Specific embodiments of the invention include a molecule capable of detecting ephrin-B2 nucleic acid wherein the molecule is a nucleic acid, a mRNA, a synthetic oligonucleotide.

Specific embodiments of the invention also include a molecule capable of detecting ephrin-B2 polypeptide wherein the molecule is a polypeptide, a synthetic polypeptide, a monoclonal antibody, an antibody fragment, a single chain fv, an EphB4-Fc receptorbody polypeptide or an EphB4 receptor fragment polypeptide containing an ephrin-B2 binding.

The subject invention provides for methods of detecting an imaging agent using, for example, a conventional scintillation camera, a gamma camera, a rectilinear scanner, a PET scanner, a SPECT scanner, a MRI scanner, a NMR scanner, an X-ray machine, or an infrared scanner.

The subject invention also provides for imaging agents which are radionuclides or chelates.

The subject invention further provides for agents capable of causing tumor cell death and vascular endothelial cell death.

The subject invention also provides for a method of delivering an agent to the vasculature of a mammal comprising administering to the mammal a composition which comprises a molecule capable of localizing to a cell expressing ephrinB2 polypeptide, wherein the molecule is coupled to the agent.

In preferred embodiments the agent is capable of stimulating angiogenesis, is capable of preventing restenosis of a blood vessel, is capable of dissolving a blood clot in a blood vessel, or is capable of reducing atherosclerotic plaques.

BRIEF DESCRIPTION OF THE FIGURE

FIGS. 1A–1G are from ephrin-B2/LacZ mice.

FIGS. 1A–1B: ephrin-B2/LacZ is strongly expressed during physiological maturing ovarian follicles (FIG. 1A) (arrows indicate capillaries) and in the neovasculature (arrowheads) of the corpus luteum after ovulation (FIG. 1B).

FIGS. 1C–1D: ephrin-B2/LacZ is strongly expressed in the neovasculature of a subcutaneously grown tumor (Lewis Lung Carcinoma). At high magnification LacZ staining is absent in veins (indicated by closed arrowheads), but found in longitudinally oriented endothelial cells (open arrowheads in FIG. 1D), also seen in a higher power view (inset).

FIGS. 1E–1G: ephrin-B2 expression in a subset of tumor endothelial cells. (FIG. 1E) Beta-galactosidase immunostaining marks a proportions of the endothelial cells labeled by PECAM (FIG. 1F). Corresponding regions between FIG. 1E and FIG. 1F indicated by white arrowheads).

FIG. 1G: In a section of tumor dual-labeled for beta-galactosidase and smooth muscle actin (SMA), ephrin-B2 activity is found in endothelial cells (green arrowheads), but not in pericytes (red arrowheads).

DETAILED DESCRIPTION OF THE INVENTION

Figures 1A, 1B, 1C, 1D, 1E, 1F, 1G:
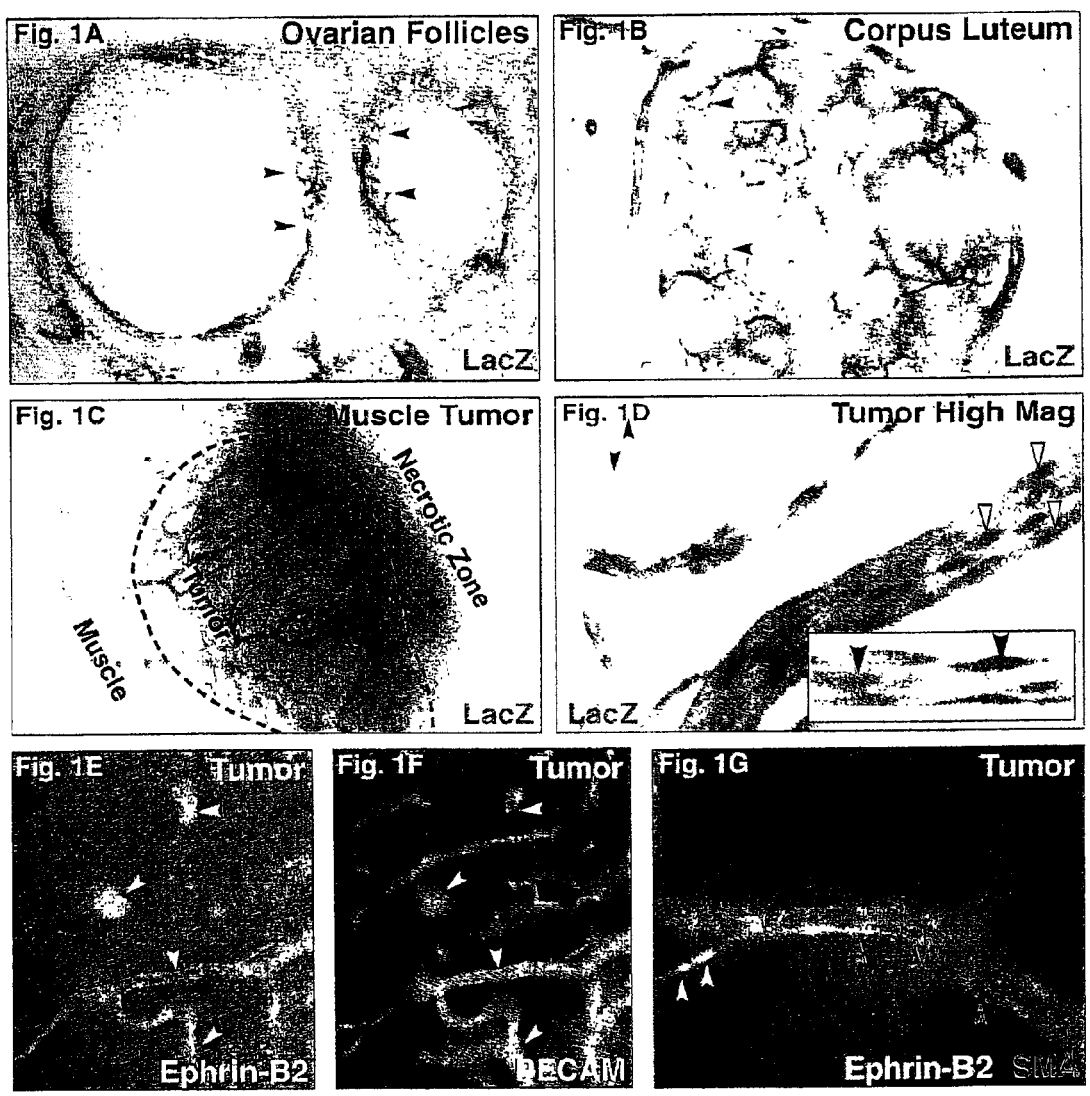
FIGS. 1A–1G. ephrin-B2 is highly expressed at sites of secondary angiogenesis in the embryo, as well as at sites of normal and pathological angiogenesis in the adult.

As ephrin-B2 appears to be an early marker of adult angiogenesis, in particular, in tumor vascularization, Applicants reasoned that imaging ephrin-B2 would be an extremely useful technique for identifying tumors at an early stage and, once identified, ephrin-B2 could be used as a target for delivering chemotherapeutic agents to the tumor site. By targeting ephrin-B2 for delivery of such an agent, one could achieve high local concentrations of the chemotherapeutic agent at the tumor site, while at the same time minimizing non-specific accumulation of the agent at non-tumor sites. Because ephrin-B2 is highly expressed in tumor vascularization, two approaches can be used to deliver the chemotherapeutic agent to the tumor site. In one embodiment of the invention, ephrin-B2 can be coupled to any chemotherapeutic agent capable of causing tumor cell death. Non-limiting examples of chemotherapeutic agents that are suitable for coupling to ephrin-B2 include carboplatin, cisplatin and other related platinum-based agents; vincristine; methotrexate; taxanes such as paclitaxel and docetaxel; fluorinated pyrimidines such as 5-fluorouracil and UFT (tegafur and uracil); hydroxyurea; gemcitabine; vinorelbine; irinotecan; tirapazamine; and matrilysin.

In an alternate embodiment of the invention, Applicants reasoned that because ephrin-B2 is highly expressed in tumor vasculature by the vascular endothelial, it is possible to deliver an agent capable of causing death of the vascular endothelial cells by coupling the agent to ephrin-B2. Vascular endothelial cell death will necessarily result in vessel regression which will ultimately lead to tumor cell death due to a lack of nutrient supply. Non-limiting examples of agents capable of causing vascular endothelial cell death that would be suitable for coupling to ephrin-B2 include gelonin, ricin A, ricin B, saporin, bryodin 1, bryodin 2, momordin, pokeweed antiviral protein from seeds (PAP-S), trichokirin, and abrin.

To image or target ephrin-B2 in tumor vasculature, it is necessary to administer a composition comprising a molecule capable of detecting ephrin-B2. Several non-limiting examples of molecules that would be suitable for detecting ephrin-B2 include EphB4-Fc receptorbody polypeptide molecules; EphB4 receptor fragment polypeptide molecules containing an ephrin-B2 binding domain; anti-ephrin-B2 monoclonal antibodies, anti-ephrin-B2 antibody fragments, anti-ephrin-B2 single chain fvs; and nucleic acids including, but not limited to, mRNAs and synthetic oligonucleotides. In fact, any molecule capable of specifically binding to or associating with ephrin-B2 would a suitable detecting molecule, including other members of the Eph family of receptor tyrosine kinases, including but not limited to EphB1, EphB2, and EphB3.

For preparation of monoclonal antibodies directed toward ephrin-B2, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy", Alan R. Liss, Inc. pp. 77–96) and the like are within the scope of the present invention.

The monoclonal antibodies for imaging or targeting use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

In addition to monoclonal antibodies, the subject application provides for fragments of such monoclonal antibodies. Antibody fragments which contain the idiotype of the antibody can be generated by known techniques. For example, such fragments include but are not limited to: the $F(ab^1)_2$ fragment which can be produced by pepsin digestion of the antibody molecule; the $Fab^1$ fragments which can be generated by reducing the disulfide bridges of the $F(ab^1)_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

In addition to monoclonal antibodies and fragments of such monoclonal antibodies, the subject application provides for single chain Fvs (scFv). A scfv is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907 assigned to Cambridge Antibody Technology Limited incorporated by reference herein.

Other suitable agents able to detect ephrin-B2 are Eph receceptorbody polypeptides, including but not limited to EphB4-Fc, EphB1-Fc, EphB2-Fc, and EphB3-Fc receptorbody polypeptides. Eph receptorbody polypeptides are secreted proteins consisting of the entire extracellular portion of the Eph receptor fused to the human immunoglobulin gamma-1 constant region (IgG1 Fc). These fusion protein would be normally expected to exist as dimers in solution based on formation of disulfide linkages between individual IgG1 Fc tails.

Suitable imaging agents that can be coupled to ephrin-B2 include, but are not limited to, agents useful in magnetic resonance imaging (MRI) such as is gadolinium chelates (see for example Ladd, DL, et al., 1999, Bioconjug Chem 10:361–370), covalently linked nonionic, macrocyclic, multimeric lanthanide chelates (see for example Ranganathan, RS, et al., 1998, Invet Radiol 33:779–797), and monoclonal antibody-coated magnetite particles (see To, SY, et al., 1992, J Clin Laser Med Surg 10:159–169). For reviews relating to basic principles of MRI see Kirsch, J E, 1991, Top Magn Reson Imaging 3:1–18 and Wallis, F and Gilbert, F J, 1999, J R Coll Surg Edinb 44:117–125. Radionuclides are also suitable imaging agents for use in nuclear medicine techniques such as positron emission tomography (PET), single positron emission computed tomography (SPECT), and computerized axial tomography (CAT) scans. By way of non-limiting example, such agents include technetium 99m, gallium 67 citrate, iodine 123 and indium 111 (see Coleman, R E, 1991, Cancer 67:1261–1270). Other radionuclides suitable as imaging agents include $^{123}$I and $^{111}$In-DTPA (see Kaltsas, Ga., et al., 1998, Clin Endocrinol (Oxf) 49;685–689), radiolabeled antibodies (see Goldenberg, DM and Nabi, HA, 1999, Semin Nucl Med 29:41–48 and Steffens, MG, et al., 1999, J Nucl Med 40:829–836). For reviews relating to basic principles of radionuclear medicine techniques, see Schiepers, C. And Hoh, CK, 1998, Eur Radiol 8:1481–1494 and Ferrand, SK, et al., 1999, Surg Oncol Clin N Am 8:185–204.

In addition, the ephrin-B2 can be administered in any one of a number of ways including, but not limited to, intramuscular, intravenous, intrarterial, subcutaneous, intrathecal, or intraperitoneal injection.

Before the present methods and kits for making and using the invention are described, it is to be understood that the invention is not to be limited only to the particular methods or kits described. The method and kits may vary, and the terminology used herein is for the purpose of describing particular embodiments. The terminology and definitions are not intended to be limiting since the scope of protection will ultimately depend upon the claims.

EXAMPLES

I. Materials and Methods:

A. Targeting Vector Construction and Embryonic Stem (ES) Cell Manipulations.

The 5' and 3' ephrin-B2 gene fragments used in the construction of the targeting vector were isolated from a 129SV mouse genomic library in the lambda Fixll vector (Stratagene, La Jolla, Calif.). The 5' region of homology incorporated in the targeting construct consisted of a 6.7 Kb Eag1 restriction fragment derived from an ephrin-B2 genomic clone (the 5' Eag1/Not1 site was contributed by the lambda Fixll phage from which this fragment was obtained), which terminated at its 3' end 51 nucleotides upstream of the ephrin-B2 start codon. This fragment was cloned into a Not1 site upstream of a promoterless LacZ CDNA in the vector pKOVpLacZ, which is comprised of the LacZ gene followed by the phosphoglycerate kinase promoter driven neomycin resistance (Neo) gene (PGK-Neo) (Suri et al., 1996). A 3' region of homology consisting of a 2 Kb Eag1-Xba1 fragment, which terminates at its 5' end approximately 100 nucleotides downstream of intron1/exon1 boundary, was subcloned into a Hindlll site of pKOVpLacZ between the PGK-Neo and HSV-tk expression units using Hindlll linkers (Suri et al., 1996). In this targeting scheme 281 nucleotides of the ephrin-B2 gene, including the transcriptional start site and signal sequence were deleted and replaced by the LacZ and Neo genes. Gene targeting in ES cells and mice derived from them were confirmed by southern blotting. Faithful expression of the LacZ gene, driven by the endogenous ephrin-B2 gene promoter, was confirmed by immunohistochemical and in situ hybridization analysis. The lacZ labeled ephrin-B2 gene was bred into C57BU6 and FVB/N strains of mice.

B. Tumor Models

Lewis Lung carcinoma cells ($5 \times 10^5$) were injected under the dorsal skin of syngeneic adult ephrin-B2 heterozygous mice. 10 to 14 days post-implantation a palpable tumor could be visualized under the skin at the injection site. In some cases subcutaneously injected tumor cells formed tumors within the thigh or flank muscle adjacent to the injection site, allowing the evaluation of both subcutaneous and intramuscular tumors.

C. Imaging the Vasculature

Generally the vasculature was made visible by visualization in tissue sections using the following procedure. Tissues was infiltrated overnight with 30% sucrose, frozen in Tissue-Tek OCT compound (Sakura Finetek, Torrance, Calif.) and sectioned with a cryostat at a thickness of 100 microns. LacZ activity was detected histochemically by X-Gal staining as described previously (Suri et al., 1996).

For immunofluorescent detection, tissues were fixed by vascular perfusion of 2% paraformaldehyde and washed with several rinses of PBS. Sections were incubated in 5% normal goat serum at room temperature for 1 hr followed by 12–15 hr in primary antibody solution in PBS/Triton. PECAM (CD31) immunoreactivity was detected by a rat anti-mouse CD31 monoclonal antibody (Pharmingen, San Diego, Calif.) diluted 1:500, followed by 4 hr in Cy3-labeled goat secondary anti-rat IgG antibody (Jackson ImmunoResearch, West Grove, Pa.) diluted 1:200 in PBS/Triton. ephrin-B2 LacZ activity was detected by a rabbit polyclonal antibody (5 Prime, 3 Prime, Boulder, Colo.) diluted 1:1000, followed by 4 hr in FITC-labeled goat secondary anti-rabbit IgG antibody. Alpha smooth muscle actin was detected with a Cy3-labeled mouse monoclonal antibody (Sigma) diluted 1:1000. For DAB immunohistochemistry antibodies to PECAM (see above) and aSMA/HRP (Dako Corp., Carpinteria, Calif.) with anti-rat biotin secondary antibodies (Vector Labs, Burlingame, Calif.) at a 1:500 dilution.

II. Results

By examining the distribution of the LacZ reporter in whole mounts and in histological sections prepared from numerous adult organs, Applicants found that ephrin-B2 expression specifically marks arterial as opposed to venous vessels in the adult. Furthermore, ephrinB2 expression is upregulated in situations of new blood vessel formation (angiogenesis).

To examine the expression of ephrin-B2 during pathologic angiogenesis, subcutaneous tumors were examined. In a dramatic example of one such tumor that had invaded the underlying muscle, it can be seen that certain vessels growing into the tumor from the surrounding muscle express high levels of ephrin-B2 (FIG. 1C). Consistent with the notion that ephrin-B2 marks arterial and not venous vessels, these tumor vessels appear to arise from previously existing ephrin-B2-expressing arterioles within the muscle (FIG. 1C). These data suggest that tumor vessels, which were previously assumed to consist of homogenous capillaries based on their small size and paucity of smooth muscle investiture (e.g. Folkman, 1971), may be divided into microvessels with either arterial or venous identity. Further consistent with this notion, it is clear that only a subset of the new tumor vessels are ephrin-B2 positive (FIG. 1D–F). Finally, ephrin-B2 was expressed by the endothelium of tumor vessels (FIG. 1D and 1G); smooth muscle cells associated with tumor vessels clearly did not express ephrin-B2.

In adult settings of physiologic and pathologic angiogenesis, such as during remodeling of the female reproductive system or in tumors, ephrin-B2 seems to recapitulate its earliest patterns of embryonic expression. That is, ephrin-B2 is highly expressed by the endothelium of some angiogenic vessels and their sprouts, and is largely lacking from the few smooth muscle cells that are associated with new vessels. The finding that angiogenic sprouts at sites of adult neovascularization have arterial identity challenges prevailing views that these sprouts largely derive from post-capillary venules and lack arterial identity (Gimbrone et al., 1974; Grunt et al., 1986a; Grunt et al., 1986b). Instead, Applicants data suggests that adult angiogenic signals cause recapitulation of an embryonic process in which ephrin-B2 might initially be involved in arterial sprouting and perhaps in anastomoses with EphB4-expressing venous sprouts, followed by playing a role in maturation of the arterial vessels by regulating formation of the muscle wall.

We claim:

1. A method of causing tumor cell death by targeting tumor vasculature, comprising administering to a mammal a composition which comprises a molecule that detects ephrin-B2 coupled to an agent that causes tumor cell death, wherein the agent that causes tumor cell death is carboplatin, cisplatin, vincristine, methotrexate, paclitaxel, docetaxel, 5-fluorouracil, UFT, hydroxyurea, gemcitabine, vinorelbine, irinotecan, tirapazamine, or matrilysin, and the molecule that detects ephrin-B2 is a nucleic acid or a polypeptide.

2. A method of causing vascular endothelial cell death by targeting tumor vasculature, comprising administering to a mammal a composition which comprises a molecule that detects ephrin-B2 coupled to an agent that causes vascular endothelial cell death, wherein the agent that causes vascular endothelial cell death is gelonin, ricin A, ricin B, saporin, bryodin 1, bryodin 2, momordin, pokeweed antiviral protein from seeds (PAP-S), trichokirin, or abrin, and the molecule that detects ephrin-B2 is a nucleic acid or a polypeptide.

3. The method of claim 1, or 2, wherein the mammal is a human.

4. The method of claim 1 or 2, wherein the polypeptide is selected from the group consisting of a monoclonal antibody, antibody fragment, single chain fv, EphB1-Fc, EphB2-Fc, EphB3-Fc, EphB4-Fc, EphB1-Fc, EphB2-Fc, EphB3-Fc, and an EphB4receptor fragment polypeptide containing an ephrin-B2 binding domain.

5. The method of claim 1 or 2, wherein the polypeptide is a synthetic polypeptide.

6. The method of claim 1 or 2, wherein the composition is administered to a mammal with a carrier suitable for parenteral administration.

7. The method of claim 1 or 2, wherein the nucleic acid is an mRNA or a synthetic oligonucleotide.

8. A kit for causing tumor cell death by targeting tumor vasculature in a mammal comprising a composition which comprises a molecule that detects ephrin-B2 coupled to an agent that causes tumor cell death, wherein the agent that causes tumor cell death is carboplatin, cisplatin, vincristine, methotrexate, paclitaxel, docetaxel, 5-fluorouracil, UFT, hydroxyurea, gemcitabine, vinorelbine, irinotecan, tirapazamine, or matrilysin, and the molecule that detects ephrin-B2 is a nucleic acid or a polypeptide.

9. A kit for causing tumor vascular endothelial cell death by targeting tumor vasculature in a mammal comprising a composition which comprises a molecule that detects ephrin-B2 coupled to an agent that causes vascular endothelial cell death, wherein the agent that causes vascular endothelial cell death is gelonin, ricin A, ricin B, saporin, bryodin 1, bryodin 2, momordin, pokeweed antiviral protein from seeds (PAP-S), trichokirin, or abrin, and the molecule that detects ephrin-B2 is a nucleic acid or a polypeptide.

* * * * *